United States Patent [19]

Bondinell et al.

[11] 4,228,170
[45] Oct. 14, 1980

[54] 7- AND/OR 8-SULFUR SUBSTITUTED 1,2,3,4-TETRAHYDROISOQUINOLINE COMPOUNDS

[75] Inventors: William E. Bondinell, Cherry Hill, N.J.; Robert G. Pendleton, Philadelphia, Pa.

[73] Assignee: SmithKline Corporation, Philadelphia, Pa.

[21] Appl. No.: 71,203

[22] Filed: Aug. 30, 1979

[51] Int. Cl.$^2$ ................... A61K 31/47; C07D 217/02
[52] U.S. Cl. ..................................... 424/258; 546/150
[58] Field of Search ........................ 546/150; 424/258

[56] References Cited

U.S. PATENT DOCUMENTS

| | | | |
|---|---|---|---|
| 3,362,956 | 1/1968 | Archer | 544/363 |
| 3,725,388 | 4/1973 | Grell et al. | 424/258 |
| 3,939,164 | 2/1976 | Kaiser et al. | 424/258 |
| 3,988,339 | 10/1976 | Kaiser et al. | 424/258 |

Primary Examiner—Paul M. Coughlan, Jr.
Attorney, Agent, or Firm—Joseph A. Marlino; William H. Edgerton; Richard D. Foggio

[57] ABSTRACT 1,2,3,4-Tetrahydroisoquinoline compounds having 7- and/or 8-sulfur substituents are inhibitors of phenylethanolamine N-methyltransferase.

13 Claims, No Drawings

7- AND/OR 8-SULFUR SUBSTITUTED 1,2,3,4-TETRAHYDROISOQUINOLINE COMPOUNDS

This invention relates to new 1,2,3,4-tetrahydroisoquinoline compounds having 7- and/or 8-sulfur substituents. These compounds have pharmacological activity, in particular they inhibit the enzyme phenylethanolamine N-methyltransferase.

Epinephrine is a hormone, synthesized in the adrenal medulla, which is released into the blood stream in response to stress and produces profound physiological changes which serve to prepare the animal to cope with the stressor situation. For example, epinephrine produces anxiety, an increase in blood pressure, acceleration of heart rate and increase in cardiac output. These changes are detrimental in individuals with certain disease conditions such as angina pectoris, myocardial infarction and anxiety neuroses.

Phenylethanolamine N-methyltransferase catalyzes the final step in the biosynthesis of epinephrine, that is the transfer of a methyl group from S-adenosylmethionine to norepinephrine to produce epinephrine.

The compounds of this invention inhibit phenylethanolamine N-methyltransferase and thus reduce the formation of epinephrine. They are therefore useful in situations where there is overproduction of epinephrine or where epinephrine production is detrimental.

The compounds of this invention are represented by the following formula:

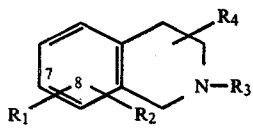

Formula 1 in which:
  $R_1$ is mercapto, methylthio, methylsulfinyl, methylsulfonyl, trichloromethylthio, trichloromethylsulfinyl, trichloromethylsulfonyl, trifluoromethylthio, trifluoromethylsulfinyl, trifluoromethylsulfonyl or fluorosulfonyl;
  $R_2$ is hydrogen, halo or trifluoromethyl with $R_1$ and $R_2$ being limited to the 7 and 8 positions and provided that when $R_1$ is methylthio $R_2$ is also methylthio;
  $R_3$ and $R_4$ are each hydrogen or lower alkyl of from one to three carbon atoms;
and pharmaceutically acceptable, acid addition salts thereof.

Preferred compounds of this invention are represented by Formula 1 when $R_1$ is defined as above, $R_2$ is chloro, and $R_3$ and $R_4$ are each hydrogen.

Advantageous compounds of this invention are represented by Formula 1 when $R_1$ is fluorosulfonyl and $R_2$, $R_3$, and $R_4$ are each hydrogen and when $R_1$ is methylthio, $R_2$ is chloro, and $R_3$ and $R_4$ are each hydrogen.

The compounds of this invention are prepared by the following procedures when 7-monosubstituted sulfur derivatives are desired.

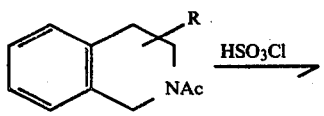

(A)

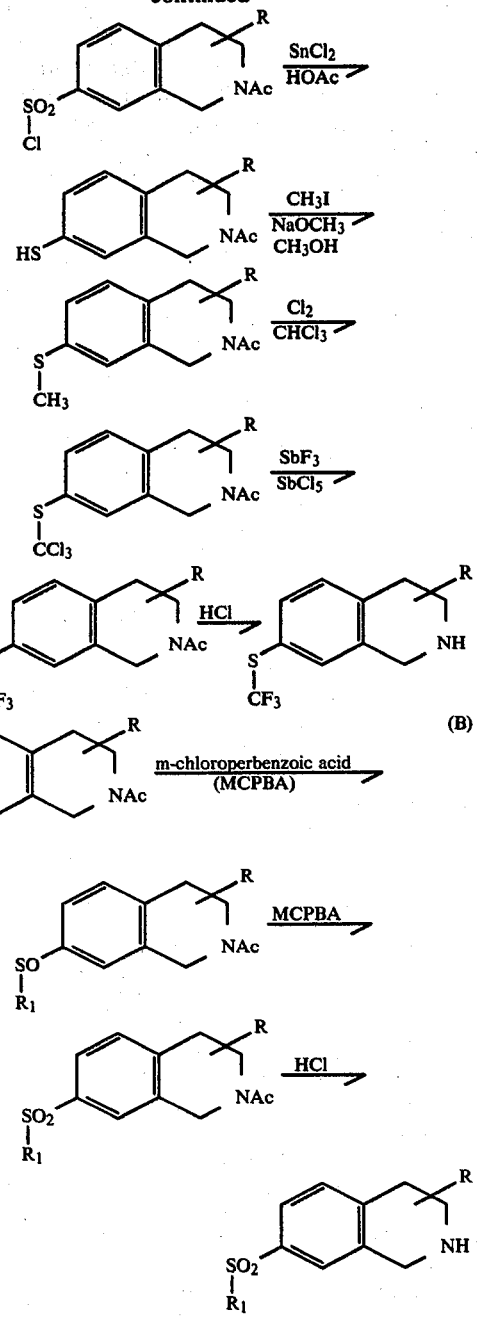

The term R being hydrogen or lower alkyl of from one to three carbon atoms and the term $R_1$ being methyl, trifluoromethyl or trichloromethyl.

According to the above procedure A, the 7-sulfur substituted tetrahydroisoquinolines are prepared by chlorosulfonating N-acyl derivatives of tetrahydroisoquinoline, for example, the N-acetyl or N-trifluoroacetyl derivatives, and then reducing the resulting sulfonyl chloride to the corresponding mercaptan derivative. The mercaptan is methylated to give the methylthio derivative which is sequentially chlorinated and fluorinated to yield the trichloromethylthio and trifluoromethylthio substituents. Following procedure B, each of the above substituents is oxidized to the corresponding sulfinyl and sulfonyl derivatives by treatment with m-chloroperbenzoic acid. Hydrolysis of the N-acyl group gives the desired 7-substituted tetrahydroisoquinoline.

The disubstituted tetrahydroisoquinolines containing a sulfur substituent and a halo or trifluoromethyl substituent are prepared from the corresponding halo or trifluoromethyl substituted mercaptans, such as N-acetyl-7(8)halo-8(7)-mercapto-1,2,3,4 tetrahydroisoquinoline. The above subsequent steps of A & B are then followed. The disubstituted mercaptans may be prepared by reacting a 7,8-dihalo, preferably dichlorotetrahydroisoquinoline with benzyl mercaptan in the presence of an organic solvent such as dimethylformamide. In the case of the N-acetyl-7,8-dihalotetrahydroisoquinoline one halo group is displaced to yield isomers of N-acetyl-7-chloro-8-mercapto or 7-mercapto-8-chloro-tetrahydroisoquinoline.

Alternatively, N-acetyl-8-chloro-7-mercapto-1,2,3,4-tetrahydroisoquinoline can be prepared by reacting 8-chloro-7-hydroxyisoquinoline with dimethylthiocarbamyl chloride and rearranging the resulting compound to 8-chloro-7-dimethylcarbamoylthioisoquinoline. This compound is hydrolyzed to give 8-chloro-7-mercaptoisoquinoline which is then reduced and acylated.

The 8-sulfur substituted tetrahydroisoquinolines are prepared from N-acetyl-8-chlorosulfonyl-tetrahydroisoquinoline and following the above procedures of A and B to get the desired products. The N-acyl-8-chlorosulfonyl derivative is prepared by diazotizing the corresponding 8-amino tetrahydroisoquinoline and treating with sulfur dioxide and cupric chloride. Similarly, 7-sulfur substituted 8-trifluoromethyl tetrahydroisoquinolines are obtained from N-acetyl-7-amino-8-trifluoromethyltetrahydroisoquinoline.

The fluorosulfonyl-tetrahydroisoquinolines are prepared by halogen exchange of the appropriate N-acyl chlorosulfonyl derivative with a fluoride, for example, potassium fluoride. This is then followed by hydrolysis of the acyl group.

N-Alkyl tetrahydroisoquinoline derivatives may be prepared by reducing the corresponding N-acyl compound with an agent such as diborane.

Pharmaceutically acceptable acid addition salts of the compounds of Formula 1, useful for the same purposes as the free base, are formed with organic and inorganic acids by methods known to the art. The base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, benzoate, ascorbate, pamoate, succinate, bismethylenesalicylate, methanesulfonate, ethanedisulfonate, benzenesulfonate, acetate, propionate, tartrate, salicylate, citrate, gluconate, lactate, malate, mandelate, cinnamate, citraconate, aspartate, stearate, palmitate, itaconate, glycolate, p-aminobenzoate, glutamate, theophylline acetates, hydrochloride, hydrobromide, sulfate, cyclohexylsulfamate, phosphate and nitrate salts.

The basic activity of the compounds of this invention is demonstrated by inhibition of phenylethanoline N-methyltransferase in vitro by the assay procedure described by Pendleton and Snow, *Molecular Pharmacology*, 9:718–725 (1973) at various compound concentrations. For example, at concentrations of $1.0 \times 10^{-4}$ and $1.0 \times 10^{-6}$ an advantageous compound of this invention, 7-fluorosulfonyl-1,2,3,4-tetrahydroisoquinoline, inhibits phenylethanolamine N-methyltransferase by 100% and 96% respectively.

The pharmaceutical compositions of this invention to inhibit phenylethanolamine N-methyltransferase comprise a pharmaceutical carrier and, as the active ingredient, a tetrahydroisoquinoline compound of Formula 1. The active ingredient will be present in the compositions of this invention in an effective amount to inhibit phenylethanolamine N-methyltransferase.

Preferably, the compositions of this invention contain the active ingredient of Formula 1 in an amount of from about 50 mg. to about 1000 mg., advantageously from about 100 mg. to about 500 mg., per dosage unit.

The pharmaceutical carrier may be for example a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example, the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of inhibiting phenylethanolamine N-methyltransferase, according to this invention, comprises administering to an animal in an amount sufficient to inhibit phenylethanolamine N-methyltransferase a tetrahydroisoquinoline compound of Formula 1.

Preferably, the compounds of Formula 1 are administered in conventional dosage unit forms prepared by combining an appropriate dose of the compound with standard pharmaceutical carriers.

Preferably, the active ingredient of Formula 1 will be administered in a daily dosage regimen of from about 100 mg. to about 2000 mg., most preferably from about 200 mg. to about 1000 mg. Advantageously, equal doses will be administered preferably two to three times per day. When the administration is carried out as described above, inhibition of phenylethanolamine N-methyltransferase is produced.

The route of administration of the pharmaceutical compositions of this invention and in accordance with the methods of this invention is internal, either parenteral or preferably oral, in an amount to produce the desired biological activity.

The following examples are not limiting but are illustrative of the compounds of this invention and processes for their preparation.

EXAMPLE 1

N-Acetyl-1,2,3,4-tetrahydroisoquinoline (180 gm., 1.03 m.) was added slowly to 800 gms. (6.9 m.) of chlorosulfonic acid and stirred at $-50°$ C. The solution was stirred at 25° C. for two days, poured onto crushed ice and extracted with ethyl acetate. The extract was washed, dried over anhydrous sodium sulfate and evaporated to yield crude N-acetyl-7-chlorosulfonyl-1,2,3,4-tetrahydroisoquinoline.

The above prepared chlorosulfonyl compound (2.2 gm., 0.008 m.) was dissolved in 75 ml. of warm glacial acetic acid and treated with 11.25 gms. (0.05 m.) of stannous chloride dihydrate at 75° in 10 ml. of concentrated hydrochloric acid. The reaction was allowed to cool to 25°, stirred for 1.5 hours and poured into 250 ml. of water containing concentrated hydrochloric acid. N-Acetyl-7-mercapto-1,2,3,4-tetrahydroisoquinoline was isolated by filtration and dried. The N-acetyl mercapto compound was hydrolyzed in refluxing 10% hydrochloric acid to give 7-mercapto-1,2,3,4-tetrahydroisoquinoline hydrochloride.

EXAMPLE 2

A suspension of N-acetyl-7-mercapto-1,2,3,4-tetrahydroisoquinoline (1.0 gm., 0.0048 m.) in 20 ml. of methanol was stirred in a nitrogen atmosphere. Sodium methoxide (0.3 gm., 0.0055 m.) and 5 ml. of iodomethane were added to the suspension. The mixture was stirred at 25° C. for thirty minutes, evaporated and partitioned between chloroform and water. The chloroform layer was washed, dried over sodium sulfate and evaporated. The residue was chromatographed on silica gel, eluted with ethyl acetate to give pure N-acetyl-7-methylthio-1,2,3,4-tetrahydroisoquinoline.

The above acetyl derivative (2.5 gm., 0.011 m.) was refluxed in 25 ml. of 10% hydrochloric acid, cooled, extracted with ethyl acetate and concentrated to dryness. The residue was recrystallized from ethanol-ethyl acetate to give 7-methylthio-1,2,3,4-tetrahydroisoquinoline hydrochloride, m.p. 247°-248° C.

EXAMPLE 3

A solution of N-acetyl-7-methylthio-1,2,3,4-tetrahydroisoquinoline, (2 gm., 0.009 m.) in 20 ml. of chloroform was cooled to $-20°$ C. and treated with (1.6 gm., 0.009 m.) m-chloroperbenzoic acid. The reaction mixture was allowed to warm to 25° C. and was washed with 10% aqueous sodium carbonate, dried over sodium sulfate and evaporated to yield N-acetyl-7-methylsulfinyl-1,2,3,4-tetrahydroisoquinoline. This compound was hydrolyzed following the procedure set forth in Example 1 to yield 7-methylsulfinyl-1,2,3,4-tetrahydroisoquinoline hydrochloride, m.p. 200°-202° C. from ethanol-ethyl acetate.

EXAMPLE 4

A solution of N-acetyl-7-methylthio-1,2,3,4-tetrahydroisoquinoline (2.0 gm., 0.009 m.) in 20 ml. of chloroform was treated with (3.2 gm., 0.018 m.) m-chloroperbenzoic acid. The reaction mixture was stirred at 25° C. washed with 5% aqueous sodium carbonate, dried over sodium sulfate and evaporated. The residue was chromatographed on silica gel eluted with ethanol-ethyl acetate (1:9) to yield N-acetyl-7-methylsulfonyl-1,2,3,4-tetrahydroisoquinoline which was hydrolyzed and crystallized from 10% hydrochloric acid to yield 7-methylsulfonyl-1,2,3,4-tetrahydroisoquinoline hydrochloride, m.p. 258°-260° C.

EXAMPLE 5

N-Acetyl-7-methylthio-1,2,3,4-tetrahydroisoquinoline, (11 gm., 0.05 m.) was dissolved in 250 ml. of ethanol-free chloroform containing 10 gm. of cumene and stirred in the dark. Chlorine was passed through the solution for two days. The solvent was evaporated and the residue was chromatographed on silica gel, eluted with ethyl acetate to give N-acetyl-7-trichloromethylthio-1,2,3,4-tetrahydroisoquinoline. Following the procedure of Example 1, hydrolysis yielded 7-trichloromethylthio-1,2,3,4-tetrahydroisoquinoline.

EXAMPLE 6

N-Acetyl-7-trichloromethylthio-1,2,3,4-tetrahydroisoquinoline (5.5 gm., 0.017 m.) was oxidized following the procedure of Example 3. The residue was chromatographed on silica gel, eluted with ethyl acetate to yield N-acetyl-7-trichloromethylsulfinyl-1,2,3,4-tetrahydroisoquinoline which was hydrolyzed and recrystallized from methanol-ether to give 7-trichloromethylsulfinyl-1,2,3,4-tetrahydroisoquinoline hydrochloride, m.p. 218°-220° C.

EXAMPLE 7

By the procedure of Example 4, N-acetyl-7-trichloromethylthio-1,2,3,4-tetrahydroisoquinoline was converted to 7-trichloromethylsulfonyl-1,2,3,4-tetrahydroisoquinoline.

The above base was converted to the maleate salt by reacting 1.0 gm. in ethanol with a molar equivalent amount of maleic acid and recrystallizing the maleate salt from methanol and ethyl acetate to yield 7-trichloromethylsulfonyl 1,2,3,4-tetrahydroisoquinoline maleate, m.p. 159°-160° C.

EXAMPLE 8

A mixture of N-acetyl-7-trichloromethylthio-1,2,3,4-tetrahydroisoquinoline (5.0 gm., 0.016 m.), antimony trifluoride (15 gm., 0.085 m.) and antimony pentachloride, (1.5 gm., 0.005 m.) was heated and stirred at 90° C. for one day. The resulting tar was partitioned between chloroform and 3 N hydrochloric acid. The chloroform extract was dried over sodium sulfate and evaporated to give N-acetyl-7-trifluoromethylthio-1,2,3,4-tetrahydroisoquinoline which was hydrolyzed following the procedure of Example 1 and the residue recrystallized from chloroform-cyclohexane and then from isopropanol-cyclohexane to give 7-trifluoromethylthio-1,2,3,4-tetrahydroisoquinoline hydrochloride, m.p. 190°-191° C.

EXAMPLE 9

Following the procedure of Example 3, N-acetyl-7-trifluoromethylthio-1,2,3,4-tetrahydroisoquinoline (5.1 gm., 0.018 m.) was oxidized and chromatographed to yield N-acetyl-7-trifluoromethylsulfinyl-1,2,3,4-tetrahydroisoquinoline which was hydrolyzed following the procedure of Example 1 and crystallized from methanol-ether to yield 7-trifluoromethylsulfinyl-1,2,3,4-tetrahydroisoquinoline hydrochloride, m.p. 205°-206° C.

EXAMPLE 10

By the procedure of Example 4, N-acetyl-7-trifluoromethylthio-1,2,3,4-tetrahydroisoquinoline (5.0 g., 0.0175 m.) was oxidized and chromatographed on silica gel eluted with ethyl acetate to give N-acetyl-7-trifluoromethylsulfonyl-1,2,3,4-tetrahydroisoquinoline. The compound was then hydrolyzed following the procedure of Example 1 and recrystallized from isopropanol-ether and acetonitrile-ethyl acetate. The hydrochloride salt was converted to the fumarate salt which was recrystallized from methanol-ethyl acetate, m.p. 199°-200° C.

EXAMPLE 11

A solution (1.9 gm., 0.01 m.) of N-acetyl-8-amino-1,2,3,4 tetrahydroisoquinoline in 10 ml. of concentrated hydrochloric acid is stirred and then cooled to 0° C. The solution is then diazotized by the addition of (0.9 gm., 0.013 m.) sodium nitrite dissolved in 6 ml. of water. The solution of the diazonium salt is added to a mixture of 9 ml. of dioxane saturated with sulfur dioxide containing (1.2 gm., 0.016 m.) potassium chloride and (0.9 gm., 0.004 m.) cupric chloride dihydrate. The mixture is stirred at 25° C. for one hour and then at 40°–60° C. for thirty minutes. The mixture is diluted with water, extracted with ethyl acetate and the solvent is evaporated to yield N-acetyl-8-chlorosulfonyl-1,2,3,4-tetrahydroisoquinoline.

Following the procedures of Examples 1 through 10 and Example 19 and substituting N-acetyl-8-chlorosulfonyl-1,2,3,4 tetrahydroisoquinoline for the 7-chlorosulfonyl derivative yields the following respective products:

8-mercapto-1,2,3,4-tetrahydroisoquinoline
8-methylthio-1,2,3,4-tetrahydroisoquinoline
8-methylsulfinyl-1,2,3,4-tetrahydroisoquinoline
8-methylsulfonyl-1,2,3,4-tetrahydroisoquinoline
8-trichloromethylthio-1,2,3,4-tetrahydroisoquinoline
8-trichloromethylsulfinyl-1,2,3,4-tetrahydroisoquinoline
8-trichloromethylsulfonyl-1,2,3,4-tetrahydroisoquinoline
8-trifluoromethylthio-1,2,3,4-tetrahydroisoquinoline
8-trifluoromethylsulfinyl-1,2,3,4-tetrahydroisoquinoline
8-trifluoromethylsulfonyl-1,2,3,4-tetrahydroisoquinoline
8-fluorosulfonyl-1,2,3,4-tetrahydroisoquinoline.

EXAMPLE 12

A mixture containing (100 g., 0.425 m.) 7,8-dichlorotetrahydroisoquinoline hydrochloride and (41 g., 0.5 m.) sodium acetate in 760 ml. of acetic acid and 430 ml. of acetic anhydride was heated at 100° C. with stirring for four hours. The cooled reaction mixture was diluted with 800 ml. of water and brought to pH 8 by addition of 5% aqueous sodium carbonate (1400 ml.). The tan precipitate was collected by filtration, dried and recrystallized from isopropanol to give N-acetyl-7,8-dichloro-1,2,3,4-tetrahydroisoquinoline having a melting point of 98°–100° C.

Under an argon atmosphere, 32 g. of a 50% mineral oil dispersion of sodium hydride was washed twice with hexane to remove the mineral oil. The residual sodium hydride was stirred with dry dimethylformamide (500 ml.) and 100 ml. of benzylmercaptan in dimethylformamide was added at such a rate that hydrogen evolution remains brisk. When hydrogen evolution has ceased, N-acetyl-7,8-dichloro-1,2,3,4-tetrahydroisoquinoline (49 g., 0.20 m.) was added and the reaction was stirred for two hours. After three days at room temperature the chilled reaction mixture was treated with concentrated hydrochloric acid until the pH reached 6–7. Most of the dimethylformamide was removed under vacuum at 75° C. and the residue was stirred with 600 ml. of water and adjusted to a pH of 9 with sodium hydroxide. After extraction with ethyl acetate, the aqueous phase was chilled and acidified by the addition of concentrated hydrochloric acid. The resulting precipitate was collected by filtration, washed with acidified ice water, and dried to give N-acetyl-7-chloro-8-mercapto-1,2,3,4-tetrahydroisoquinoline, m.p. 92°–112° C.

A suspension of N-acetyl-7-chloro-8-mercapto-1,2,3,4-tetrahydroisoquinoline (1 g., 0.004 m.) in dilute hydrochloric acid was refluxed for three hours under an argon atmosphere. The reaction mixture was evaporated under reduced pressure and the residue was dried by evaporation from methanol-toluene. Recrystallization from methanol-ethyl acetate gave 7-chloro-8-mercapto-1,2,3,4-tetrahydroisoquinoline hydrochloride, m.p. 205°–207° C.

EXAMPLE 13

Sodium metal (0.115 g., 0.005 m.) was dissolved in 5 ml. of dry methanol under an argon atmosphere. N-acetyl-7-chloro-8-mercapto-1,2,3,4-tetrahydroisoquinoline (1.21 g., 0.005 m.) and (0.53 ml., 0.0045 m.) trimethylphosphate were added and the resulting mixture was stirred at reflux for three hours. The cooled reaction mixture was evaporated to a residue which was distributed between water (5 ml.) and methylene chloride (10 ml.). The methylene chloride phase was separated and the aqueous phase was extracted with additional methylene chloride. The combined organic phases were dried and evaporated and gave 1.2 g. of N-acetyl-7-chloro-8-methylthio-1,2,3,4-tetrahydroisoquinoline as a yellow oil.

A suspension of the methylthio compound (1.2 g., 0.0047 m.) in 15 ml. of dilute hydrochloric acid was heated at reflux for two and a half hours. The mixture was evaporated to a residue under reduced pressure and dried by evaporation of the residue from ethanol-toluene. Recrystallization from methanol-ethyl acetate gave 7-chloro-8-methylthio-1,2,3,4-tetrahydroisoquinoline hydrochloride, m.p. 239°–241° C.

EXAMPLE 14

To (122 g., 0.68 m.) 8-chloro-7-hydroxyisoquinoline in 180 ml. of dimethylformamide was added (450 g., 4.5 m.) triethylamine followed by (140 g., 0.87 m) dimethylthiocarbamoyl chloride. The mixture was stirred for four hours at room temperature and then poured into 5400 ml. of water. The resulting solid was collected by filtration, dried, dissolved in chloroform, dried with sodium sulfate and evaporated to yield 8-chloro-7-dimethylthiocarbamoylisoquinoline.

To 2200 ml. of Dowtherm (mixture of phenyl ether and biphenyl) at 150° C. under a nitrogen atmosphere was added (147 g., 0.55 m.) 8-chloro-7-dimethylthiocarbamoylisoquinoline in portions and the mixture was stirred. The temperature was raised to 220° C. and maintained for one hour, cooled, diluted with ether (2850 ml.) and extracted with 3 N HCl. The combined aqueous phases were washed with ether, treated with charcoal, filtered and adjusted to a pH of 6 with concentrated ammonium hydroxide. The resulting precipitate was collected by filtration, dried and recrystallized from isopropanol to give 8-chloro-7-dimethylcarbamoylthioisoquinoline, m.p. 140°–142° C.

To a stirred solution (213 g., 0.08 m.) of 8-chloro-7-dimethylcarbamoylthioisoquinoline in 750 ml of methanol was slowly added 77 ml. of 10% aqueous sodium hydroxide under a nitrogen atmosphere. The resulting solution is refluxed 1.5 hours, cooled, concentrated at reduced pressure, diluted with 90 ml. of water and adjusted to pH 6–7 with glacial acetic acid. The resulting precipitate was collected by filtration, washed with cold water and dried to yield 8-chloro-7-mercaptoisoquinoline, m.p. 118°–122° C.

To a solution of (11.7 g., 0.06 m.) 8-chloro-7-mercaptoisoquinoline in 150 ml. of methylene chloride was added a solution of 1 M borane-methylsulfide complex (120 ml., 0.12 m.). The addition was carried out dropwise with stirring under a nitrogen atmosphere. After stirring for half an hour the reaction mixture was refluxed for 2.5 hours, cooled to 5° C., and treated with 135 ml. of methanol dropwise. The reaction mixture was evaporated to a residue under reduced pressure and was then repeatedly evaporated from methanol. The residue was dissolved in methanol and treated with ethereal hydrogen chloride. The resulting precipitate was collected by filtration and dried to give 8-chloro-7-mercapto-1,2,3,4-tetrahydroisoquinoline hydrochloride, m.p. 230°–234° C. dec.

A mixture containing (14 g., 0.07 m.) 8-chloro-7-mercapto-1,2,3,4 tetrahydroisoquinoline, 62 ml. of acetic anhydride and (5.8 g., 0.07 m.) of sodium acetate in 110 ml. of acetic acid was stirred at reflux under an argon atmosphere for two hours. The cooled reaction mixture was evaporated to near dryness under reduced pressure, suspended in water and extracted with methylene chloride. The methylene chloride extracts were washed with cold aqueous sodium carbonate solution and saturated sodium chloride, dried and evaporated to an oily residue, N,S-diacetyl-8-chloro-7-mercapto-1,2,3,4-tetrahydroisoquinoline.

To a stirred solution of the above diacetyl compound (15.5 g., 0.055 m.) in 300 ml. of methanol was added 26 ml. of 10% aqueous sodium hydroxide under an argon atmosphere. After two hours at room temperature, the reaction mixture was evaporated under reduced pressure, suspended in 100 ml. of cold water, acidified with dilute hydrochloric acid and extracted with methylene chloride. The organic extracts were combined, dried and evaporated to yield N-acetyl-8-chloro-7-mercapto-1,2,3,4-tetrahydroisoquinoline as a gummy solid.

EXAMPLE 15

In the procedure of Example 13, using N-acetyl-8-chloro-7-mercapto-1,2,3,4-tetrahydroisoquinoline in place of N-acetyl-7-chloro-8-mercapto-1,2,3,4-tetrahydroisoquinoline as a starting material gave the product 8-chloro-7-methylthio-1,2,3,4-tetrahydroisoquinoline hydrochloride, m.p. 268°–270° C.

EXAMPLE 16

A solution of N-acetyl-8-chloro-7-methylthio-1,2,3,4-tetrahydroisoquinoline (0.51 g., 0.002 m.) in 15 ml. of chloroform was stirred and treated in portions with 85% of m-chloroperbenzoic acid (0.41 g., 002 m.). After stirring for eighteen hours, the solution was washed with 5% aqueous sodium bicarbonate (45 ml.), dried and evaporated to an oily residue, N-acetyl-8-chloro-7-methylsulfinyl-1,2,3,4-tetrahydroisoquinoline.

A mixture of the oily residue (1.53 g., 0.0056 m.) and dilute hydrochloric acid (24 ml.) was stirred and refluxed for three hours. The cooled reaction mixture was concentrated to a residue under reduced pressure and the residue was dried by evaporation from methanol-toluene. Recrystallization from ethanol-ether gave 8-chloro-7-methylsulfinyl-1,2,3,4-tetrahydroisoquinoline hydrochloride having a melting point of 229°–233° C. (dec.).

EXAMPLE 17

A solution of N-acetyl-8-chloro-7-methylthio-1,2,3,4-tetrahydroisoquinoline (0.51 g., 0.002 m.) in 15 ml. of chloroform was stirred and treated in portions with 85% m-chloroperbenzoic acid (1.0 g., 0.005 m.). After the solution was stirred for eighteen hours, it was washed with 5% aqueous sodium sulfite and then with 5% aqueous sodium carbonate, dried and evaporated to yield N-acetyl-8-chloro-7-methylsulfonyl-1,2,3,4-tetrahydroisoquinoline as a greasy residue.

A mixture of (1.1 g., 0.0038 m.) the above residue and dilute hydrochloric acid (15 ml.) was stirred at reflux for three hours. The cooled reaction was concentrated at reduced pressure and the residue was dried by evaporation from methanol-toluene. Recrystallization from ethanol/ether gave 8-chloro-7-methylsulfonyl-1,2,3,4-tetrahydroisoquinoline hydrochloride, m.p. 231°–236° C. (dec).

EXAMPLE 18

Following the procedure of Examples 16 and 17 and using N-acetyl-7-chloro-8-methylthio-1,2,3,4-tetrahydroisoquinoline as the starting material gives the products 7-chloro-8-methylsulfinyl-1,2,3,4-tetrahydroisoquinoline and 7-chloro-8-methylsulfonyl-1,2,3,4-tetrahydroisoquinoline respectively.

EXAMPLE 19

Trifluoroacetic anhydride (200 g.) was cooled and 26.6 g. (0.2 mole) of 1,2,3,4-tetrahydroisoquinoline was added dropwise. The solution was stirred at room temperature for three hours. The excess trifluoroacetic anhydride was distilled off at atmospheric pressure and the residue was distilled at 160° C. and 12 mm. to give 2-trifluoroacetyl-1,2,3,4-tetrahydroisoquinoline.

To a solution of 2-trifluoroacetyl-1,2,3,4-tetrahydroisoquinoline 45.84 g. (0.2 mole) in 300 ml. of chloroform was added slowly 82.4 ml. (1.24 mole) of chlorosulfonic acid. The solution was stirred and the temperature allowed to come down to 25° C. The solution was quenched in ice water and extracted with chloroform. The extract was washed with water and dried over magnesium sulfate and concentrated. The residue was treated with ether and allowed to stand overnight. The resultant solid was filtered off, added to chloroform, cooled, treated with ether and allowed to stand in the cold for several hours. The resultant solid was again taken up in chloroform and treated with ether to give 2-trifluoroacetyl-7-chlorosulfonyl-1,2,3,4-tetrahydroisoquinoline, m.p. 108°–109° C.

A mixture of the above 7-chlorosulfonyl compound 1.0 g. (0.0031 mole) in 10 ml. of acetone and 2.0 ml. of an aqueous solution containing 1.46 g. (0.025 mole) of potassium fluoride was stirred at room temperature for abour 18 hours. The mixture was then concentrated to dryness and the residue taken up in chloroform, washed with water, dried over magnesium sulfate and concentrated to yield 2-trifluoroacetyl-7-fluorosulfonyl-1,2,3,4-tetrahydroisoquinoline, m.p. 99°–103° C.

A solution of 5.0 g. (0.06 mole) of 2-trifluoroacetyl-7-fluorosulfonyl-1,2,3,4-tetrahydroisoquinoline and 100 ml. of acetone and 50 ml. of 6 N hydrochloric acid was stirred at room temperature overnight. The solution was concentrated, taken up in water, extracted with chloroform, concentrated and the water azeotropically removed. The resultant solid was recrystallized from methanol to give 7-fluorosulfonyl-1,2,3,4-tetrahydroisoquinoline hydrochloride, m.p. 230°–232° C.

EXAMPLE 20

7-Amino-8-trifluoromethyl-1,2,3,4-tetrahydroisoquinoline (8.7 g., 0.04 m.) is treated with isopropenyl acetate (8.0 g., 0.08 m.) in refluxing ethyl acetate to give N-acetyl-7-amino-8-trifluoromethyl-1,2,3,4-tetrahydroisoquinoline.

Following the procedure of Example 11 the above compound is converted to N-acetyl-7-chlorosulfonyl-8-trifluoromethyl-1,2,3,4-tetrahydroisoquinoline which is then, according to Examples 1 through 10 and 19, converted to the following:
7-mercapto-8-trifluoromethyl-1,2,3,4-tetrahydroisoquinoline
7-methylthio-8-trifluoromethyl-1,2,3,4-tetrahydroisoquinoline
7-methylsulfinyl-8-trifluoromethyl-1,2,3,4-tetrahydroisoquinoline
7-methylsulfonyl-8-trifluoromethyl-1,2,3,4-tetrahydroisoquinoline
7-trichloromethylthio-8-trifluoromethyl-1,2,3,4-tetrahydroisoquinoline
7-trichloromethylsulfinyl-8-trifluoromethyl-1,2,3,4-tetrahydroisoquinoline
7-trichloromethylsulfonyl-8-trifluoromethyl-1,2,3,4-tetrahydroisoquinoline
7-trifluoromethylthio-8-trifluoromethyl-1,2,3,4-tetrahydroisoquinoline
7-trifluoromethylsulfinyl-8-trifluoromethyl-1,2,3,4-tetrahydroisoquinoline
7-trifluoromethylsulfonyl-8-trifluoromethyl-1,2,3,4-tetrahydroisoquinoline
7-fluorosulfonyl-8-trifluoromethyl-1,2,3,4-tetrahydroisoquinoline

EXAMPLE 21

N-Acetyl-8-chloro-7-mercapto-1,2,3,4-tetrahydroisoquinoline (24 g., 0.1 m.) is dissolved in tetrahydrofuran and treated with 300 ml. of 1 M diborane (0.3 m.). The mixture is refluxed, cooled, treated with water and then aqueous hydrochloric acid and evaporated to yield 8-chloro-N-ethyl-7-mercapto-1,2,3,4-tetrahydroisoquinoline hydrochloride.

EXAMPLE 22

In the procedures of Examples 1 through 10 and 19 using the following compounds as starting materials:
N-acetyl-1-methyl-1,2,3,4-tetrahydroisoquinoline
N-acetyl-3-methyl-1,2,3,4-tetrahydroisoquinoline
the 1-methyl and 3-methyl-1,2,3,4-tetrahydroisoquinolines with the following groups in the 7-position are prepared:

| | |
|---|---|
| mercapto | |
| methylthio | trichloromethylsulfonyl |
| methylsulfinyl | trifluoromethylthio |
| methylsulfonyl | trifluoromethylsulfinyl |
| trichloromethylthio | trifluoromethylsulfonyl |
| trichloromethylsulfinyl | fluorosulfonyl |

EXAMPLE 23

Following the procedure of Example 14, 8-chloro-7-hydroxy-4-methylisoquinoline is converted to N-acetyl-8-chloro-7-mercapto-4-methyl-1,2,3,4-tetrahydroisoquinoline which is hydrolyzed following the procedure of Example 1 to 8-chloro-7-mercapto-4-methyl-1,2,3,4-tetrahydroisoquinoline.

EXAMPLE 24

Following the procedures of Examples 2–10, N-acetyl-8-chloro-7-mercapto-4-methyl-1,2,3,4-tetrahydroisoquinoline is converted to the following compounds:
8-chloro-7-methylthio-4-methyl-1,2,3,4-tetrahydroisoquinoline
8-chloro-7-methylsulfinyl-4-methyl-1,2,3,4-tetrahydroisoquinoline
8-chloro-7-methylsulfonyl-4-methyl-1,2,3,4-tetrahydroisoquinoline
8-chloro-7-trichloromethylthio-4-methyl-1,2,3,4-tetrahydroisoquinoline
8-chloro-7-trichloromethylsulfinyl-4-methyl-1,2,3,4-tetrahydroisoquinoline
8-chloro-7-trichloromethylsulfonyl-4-methyl-1,2,3,4-tetrahydroquinoline
8-chloro-7-trifluoromethylthio-4-methyl-1,2,3,4-tetrahydroisoquinoline
8-chloro-7-trifluoromethylsulfinyl-4-methyl-1,2,3,4-tetrahydroisoquinoline
8-chloro-7-trifluoromethylsulfonyl-4-methyl-1,2,3,4-tetrahydroisoquinoline

EXAMPLE 25

A solution of lithium methylmercaptide (3.0 ml.) in dimethylformamide was diluted with 2.0 ml. of dimethylformamide and 200 mg. (1.01 mm.) of 7,8-dichloroisoquinoline was added. The reaction was stirred at room temperature under nitrogen for thirty minutes. The mixture was taken up in 100 ml. of ethyl acetate washed with 3 separate 100 ml. portions of aqueous sodium chloride and dried over magnesium sulfate. The solvent was removed and the residue was taken up in ether and treated with hydrochloric acid and ether. The resulting solid was recrystallized from methanol-ether to yield 7,8-bismethylthioisoquinoline having a melting point of 255°–257° C. (dec.).

7,8-Bismethylthioisoquinoline (553 mg., 2.5 mm.) was dissolved in 25 ml. of methylene chloride and 8 ml. of a solution of 1 M borane-dimethylsulfide complex in methylene chloride. The solution was refluxed under argon for eighteen hours and allowed to stand at room temperature overnight. The excess hydride was destroyed with methanol and the volatiles stripped off. The residual solid was treated with methanol and then refluxed for one hour in 20 ml of hydrochloric acid/methanol. The volatiles were evaporated and the resulting semi-solid was converted to the free base with sodium hydroxide-methylene chloride and chromatographed on silica gel employing 10% methanol-methylene chloride as the eluent. The resulting oil was dissolved in methanol and treated with hydrochloric acid ether to yield a white solid which was recrystallized in methanol to yield 7,8-bismethylthiotetrahydroisoquinoline hydrochloride having a melting point of 247°–249° C. (dec.).

EXAMPLE 26

| Ingredients | Amounts |
|---|---|
| 7-fluorosulfonyl-1,2,3,4-tetrahydroisoquinoline hydrochloride | 150 m |
| Lactose | 350 m |

The ingredients are mixed and filled into a hard gelatin capsule.

EXAMPLE 27

| Ingredients | Amounts |
| --- | --- |
| 7-methylthio-8-chloro-1,2,3,4-tetrahydroisoquinoline | 200 mg. |
| Calcium sulfate dihydrate | 150 mg. |
| Surcose | 25 mg. |
| Starch | 15 mg. |
| Talc | 5 mg. |
| Stearic Acid | 3 mg. |

The calcium sulfate dihydrate, sucrose and the tetrahydroisoquinoline are thoroughly mixed and granulated with 10% gelatin solution. The wet granules are screened, dried and then mixed with the starch, talc and stearic acid, screened and compressed into a tablet.

One tablet is administered three times a day.

What is claimed is:

1. A compound of the formula:

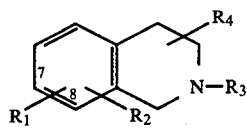

in which:

$R_1$ is mercapto, methylthio, methylsulfinyl, methylsulfonyl, trichloromethylthio, trichloromethylsulfinyl, trichloromethylsulfonyl, trifluoromethylthio, trifluoromethylsulfinyl, trifluoromethylsulfonyl or fluorosulfonyl;

$R_2$ is hydrogen, halo or trifluoromethyl and provided that when $R_1$ is methylthio $R_2$ is also methylthio, with $R_1$ and $R_2$ being limited to the 7 and 8 positions;

$R_3$ and $R_4$ are each hydrogen or lower alkyl;

or a pharmaceutically acceptable acid addition salt thereof.

2. The compound of claim 1 in which $R_2$, $R_3$ and $R_4$ are hydrogen.

3. The compound of claim 2 in which $R_1$ is in the 7-position.

4. The compound of claim 1 in which $R_2$ is 8-chloro and $R_3$ and $R_4$ are hydrogen.

5. The compound of claim 3 in which $R_1$ is 7-fluorosulfonyl, being the compound 7-fluorosulfonyl-1,2,3,4-tetrahydroisoquinoline.

6. The compound of claim 4 in which $R_1$ is 7-methylthio, being the compound 8-chloro-7-methylthio-1,2,3,4-tetrahydroisoquinoline.

7. The compound of claim 1 in which $R_2$ is 7-chloro and $R_3$ and $R_4$ are hydrogen.

8. The compound of claim 7 in which $R_1$ is methylthio, being the compound 7-chloro-8-methylthio-1,2,3,4-tetrahydroisoquinoline.

9. A pharmaceutical composition in dosage unit form for inhibiting phenylethanolamine N-methyltransferase comprising a pharmaceutical carrier and an effective amount of the compound as described in claim 1.

10. A pharmaceutical composition in dosage unit form for inhibiting phenylethanolamine N-methyltransferase comprising a pharmaceutical carrier and an effective amount of the compound as described in claim 5.

11. A pharmaceutical composition in dosage unit form for inhibiting phenylethanolamine N-methyltransferase comprising a pharmaceutical carrier and an effective amount of the compound as described in claim 8.

12. A method of inhibiting phenylethanolamine N-methyltransferase which comprises administering to an animal in an amount sufficient to inhibit phenylethanolamine N-methyltransferase a compound as described in claim 1.

13. A method of inhibiting phenylethanolamine N-methyltransferase which comprises administering to an animal in an amount sufficient to inhibit phenylethanolamine N-methyltransferase a compound as described in claim 5.